(12) United States Patent
Perra et al.

(10) Patent No.: US 6,443,953 B1
(45) Date of Patent: Sep. 3, 2002

(54) SELF-ALIGNING CAP NUT FOR USE WITH A SPINAL ROD ANCHOR

(75) Inventors: Joseph Perra, Shoreview, MN (US); Rolando Puno, Prospect, KY (US); Philip A. Mellinger, Las Flores, CA (US)

(73) Assignee: Cross Medical Products, Inc., Irvine, CA (US)

( * ) Notice: Subject to any disclaimer, the term of this patent is extended or adjusted under 35 U.S.C. 154(b) by 0 days.

(21) Appl. No.: 09/518,961

(22) Filed: Mar. 6, 2000

Related U.S. Application Data

(60) Provisional application No. 60/181,010, filed on Feb. 8, 2000.

(51) Int. Cl.[7] ............................................... A61B 17/70
(52) U.S. Cl. ........................................... 606/61; 606/73
(58) Field of Search ................................ 606/60, 61, 73

(56) References Cited

U.S. PATENT DOCUMENTS

| | | | | |
|---|---|---|---|---|
| 5,005,562 A | * | 4/1991 | Cotrel | 606/61 |
| 5,261,912 A | * | 11/1993 | Frigg | 606/61 |
| 5,536,268 A | * | 7/1996 | Griss | 606/61 |
| 5,713,898 A | * | 2/1998 | Stucker et al. | 606/60 |
| 5,738,685 A | * | 4/1998 | Halm et al. | 606/61 |
| 5,752,957 A | * | 5/1998 | Ralph et al. | 606/61 |

* cited by examiner

Primary Examiner—David O. Reip
(74) Attorney, Agent, or Firm—Hudak & Shunk Co., L.P.A.; Laura F. Shunk

(57) ABSTRACT

A spinal implant system is provided having a stabilization rod, a plurality of bone anchors which could be either hooks or screws and which have an internal recess that defines a rod-receiving channel. Sidewalls of the anchor project beyond the recess, and are threaded on the outside. These external threads cooperate with the internal threads of a locking member, or cap nut, which has a top surface with a cavity that includes an internal hexagon. The internal threads are on the inside of the cylindrical sidewalls of the cap nut. Further, on the bottom side of the top surface, the cap nut has a guide member in the form of a cylindrical boss, which has a smaller diameter than that of the recess within the anchor. The boss helps to prevent cross threading and to prevent collapse of the anchor sidewalls under high forces. An annular ridge on the bottom of the boss further helps to retain the rod relative to the anchor.

11 Claims, 2 Drawing Sheets

SELF-ALIGNING CAP NUT FOR USE WITH A SPINAL ROD ANCHOR

THIS PATENT APPLICATION IS BASED UPON U.S. PROVISIONAL APPLICATION SERIAL NO. 60/181,010 FILED Feb. 8, 2000.

The invention relates generally to locking nuts for use with a spinal implant system, and more particularly to a self-aligning cap nut, which requires less clearance for tightening and further which has improved rod gripping characteristics.

BACKGROUND OF THE INVENTION

It has become an established procedure in treating certain spinal conditions to surgically implant a spinal stabilization system. Generally, these systems include two similar sets of implants, which are inserted on both sides of the spinous processes. Each set has one or more elongated rods, or plates, which span multiple vertebral bodies and secure them in alignment by means of a bone anchor member, typically a screw or a vertebral hook. The anchor may include a channel, which is intended to cradle the rod as it extends along its longitudinal axis form one anchor to the next. Finally, locking means secure the rod in the channel so that its position relative to the anchor remains fixed. The locking mechanisms include sliding members, which form a dovetail cooperation with a top opening in the anchor. Other locking members may include a threaded cooperation with the anchor, which allows the locking member to be tightened down into a secure contact with the rod.

As these implant systems may be used to correct a misalignment of the vertebral bodies, relatively large forces may act against the components. For example, the rod may be subjected to torque and/or bending, which the anchor and locking member must counter in cooperation so that the system may function as intended. Particularly strong forces are generated when a surgeon uses the system for correction of a spinal curvature, such as scoliosis.

In addition to the issues regarding the ability of the system to resist forces, these systems must be as minimal and non-invasive as possible in order to inhibit negative impact on the affected surgical area. Further, the system must be designed for ease of implantation and assembly. It is an advantage for the system to be streamlined with few parts for assembly, and with parts that go together easily and which can be disassembled as well.

The current invention provides a locking member, which can be used in conjunction with externally threaded bone anchors currently in existence. However, in order to reduce the space needed to apply the new locking member, it has an internal torque driving surface. In particular, this internal surface is a hexagonal recess, although it is envisioned that other torque receiving configurations could be used. Further, the locking member of the present invention is self-aligning so as to minimize cross threading. This is accomplished by providing an internal projection or boss, which extends into the recess of the anchor member and fills the recess above the rod channel between the sidewalls of the anchor. This projection also acts to stabilize the sides of the anchor so as to prevent the side-walls from collapsing inward at high torque forces. In addition, the projection includes a high friction surface on the bottom in order to further increase the gripping force which can be applied to the rod by the locking member or cap nut. In particular, this high friction surface is a circular ridge, which provides for two additional points of contact with the rod surface. Thus, the cap nut of the present invention grips the rod with the external edge of the nut and with the internal ridges of the projection, which contact the rod.

DETAILED DESCRIPTION OF THE INVENTION

Figure 1:
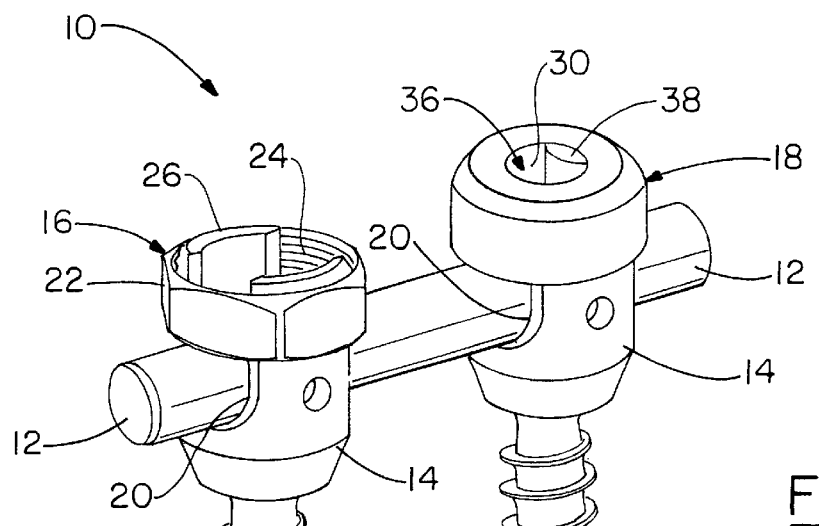
FIG. 1 is a top perspective view of a spinal system in accordance with the present invention.
Figure 2:
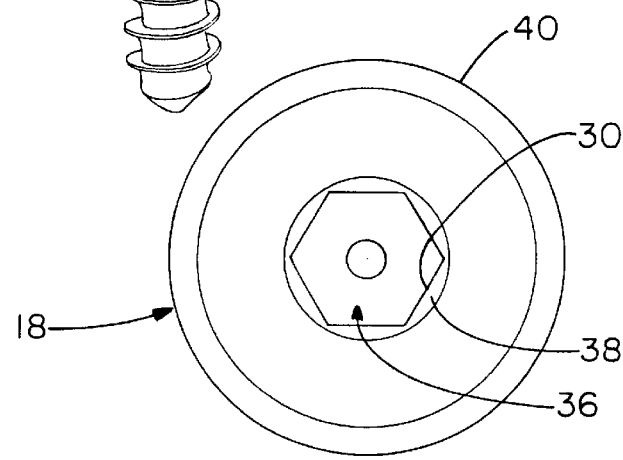
FIG. 2 is a top plan view of the locking member in accordance with the present invention.
Figure 4:
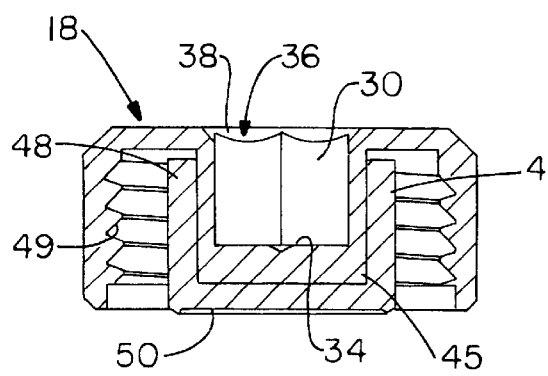
FIG. 4 is a cross-section taken along 4—4 of FIG. 3.
Figure 3:
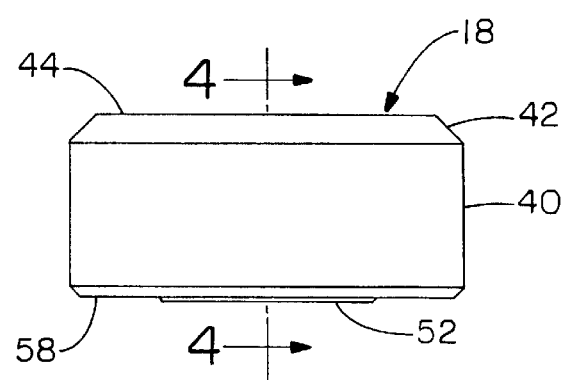
FIG. 3 is a side elevational view of the locking member in accordance with the present invention.
Figure 6:
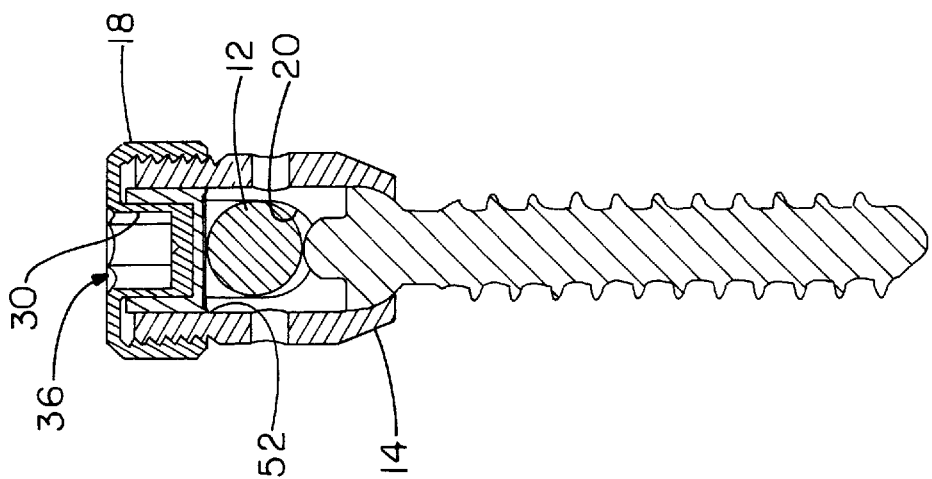
FIG. 6 is a cross-section of the assembly taken along 6—6 of FIG. 5.
Figure 5:
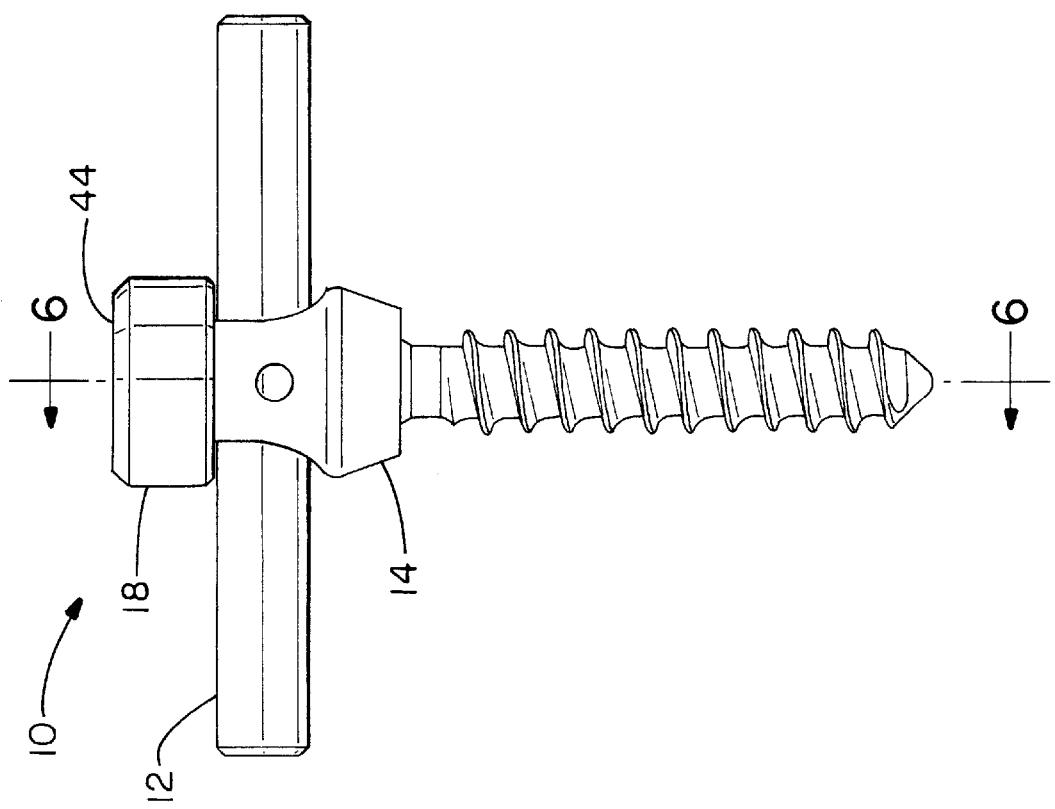
FIG. 5 is a side elevation view of an implant assembly in accordance with the present invention.

The spinal implant system 10 of the present invention is shown in FIG. 1 with an elongated cylindrical stabilization rod 12, and two rod anchors 14 each having a locking member 16, 18 which holds the rod securely in the rod channels 20 in the anchor members. The locking member 16 is a prior art locking nut. It includes an external torque-driving surface, which is an external hexagon 22. It also includes a through bore 24, which includes internal threads that mate with external threads on the side-walls 26 which extend upwardly beyond the rod channel 20 of the rod anchor 14.

The locking member, or cap nut, in accordance with the present invention has an internal torque driving surface 30. It is illustrated as an internal hexagon; however, it is within the scope of the invention to use other internal torque driving configurations, including for example key shapes, I-shapes, star shapes and the like. This enables closer positioning of adjacent anchors since it reduces the size needed for the torque-driving tool. This is intended in particular for use in the low back region. The beveled surfaces 38 of the cavity 36 framing the internal hexagon helps in seating the torque driving tool and avoids sharp edges.

The cap nut 18 has a smooth cylindrical side wall 40 joined by a beveled area 42 (which reduces the possibility of irritation to the surrounding area) to a flat top wall 44 that includes the cavity 36. On the inside, the sidewall 40 has internal threads 49, which mate with external threads on the anchor 14. These threads are illustrated as buttress threads.

Further, the cap nut has an internal recess 36. A guide member or boss 46 extends downwardly from the top wall 44. For ease of production, the boss 46 includes a sleeve 48, which extends over the projection 45 formed by the cavity 36. This provides for the proper clearance between the boss 46 and the sidewalls of the anchor. On the bottom surface 50, the boss 46 includes an annular ridge 52, which projects downwardly beyond the terminal edge 58 of the side wall 40 of the cap nut. When the cap nut is tightened onto the anchor, the ridge 52 provides for two additional points of contact with the rod surface. The terminal edge 58 of the sidewall forms a first circular gripping surface, which contacts the rod circumference. The ridge 52 forms a concentric inner gripping means, which substantially augments the ability of the cap to lock the rod in position in the anchor channel.

While in accordance with the patent statutes the best mode and preferred embodiment have been set forth, the scope of the invention is not limited thereto, but rather by the scope of the attached claims.

What is claimed is:

1. A spinal stabilization system comprising:

a bone anchor having a recess which defines a rod receiving channel and having sidewalls which extend beyond the rod receiving channel which include external threads;

a rod, and a locking member having a sidewall defining an internal recess having internal threads that mate with the external threads of the anchor, a top wall with a cavity defining an internal torque driving surface, and an integral guide member that extends downwardly from said top wall into said internal recess.

2. A spinal stabilization system as set forth in claim 1, wherein said guide member includes a bottom surface, which has a high friction surface.

3. A spinal stabilization system as set forth in claim 2, wherein said high friction surface is an annular ridge.

4. A spinal stabilization system as set forth in claim 3, wherein said internal torque surface is an internal hexagon.

5. A spinal stabilization system as set forth in claim 1, wherein said locking member is a cap nut.

6. A spinal stabilization system as set forth in claim 5, wherein the guide member extends into the internal recess beyond the termination of the internal threads.

7. A spinal stabilization system as set forth in claim 5, wherein the guide member has a bevel at its terminal end.

8. A spinal stabilization system comprising:

a bone anchor having a recess which defines a stabilizer receiving channel and having sidewalls which extend beyond the stabilizer receiving channel which include external threads;

a stabilizer, and a locking member which is a capnut having a sidewall defining an internal recess having internal threads that mate with the external threads of the anchor and that extend downwardly to a thread runout, a top wall defining a torque driving surface, and the capnut has an internal boss that extends downwardly from said top wall into said internal recess beyond the thread runout of the internal threads and which has a terminal end having an annular ridge such that the locking member has four areas of contact with the stabilizer when the system has been assembled and tightened.

9. A spinal stabilization system as set forth in claim 8, wherein said stabilizer is a rod.

10. A spinal stabilization system as set forth in claim 9, wherein the bone anchor is a screw.

11. A spinal stabilization system as set forth in claim 10, wherein the boss has a bevel at its terminal end.

* * * * *